United States Patent
Klinman et al.

(10) Patent No.: US 8,895,521 B2
(45) Date of Patent: Nov. 25, 2014

(54) METHODS AND COMPOSITIONS FOR THE TREATMENT OF UVEITIS

(75) Inventors: Dennis M. Klinman, Potomac, MD (US); Igal Gery, Bethesda, MD (US); Chiaki Fujimoto, North Bethesda, MD (US)

(73) Assignee: The United States of America as represented by the Secretary of the Department of Health and Human Services, Washington, DC (US)

(*) Notice: Subject to any disclaimer, the term of this patent is extended or adjusted under 35 U.S.C. 154(b) by 1428 days.

(21) Appl. No.: 11/579,518

(22) PCT Filed: May 5, 2005

(86) PCT No.: PCT/US2005/015761
§ 371 (c)(1),
(2), (4) Date: Nov. 17, 2008

(87) PCT Pub. No.: WO2005/115359
PCT Pub. Date: Dec. 8, 2005

(65) Prior Publication Data
US 2009/0082288 A1   Mar. 26, 2009

Related U.S. Application Data

(60) Provisional application No. 60/569,276, filed on May 6, 2004.

(51) Int. Cl.
| | | |
|---|---|---|
| C12N 15/113 | (2010.01) | |
| C07H 21/04 | (2006.01) | |
| A61K 31/7088 | (2006.01) | |
| C12N 15/117 | (2010.01) | |
| A61K 45/06 | (2006.01) | |

(52) U.S. Cl.
CPC .......... *C12N 15/117* (2013.01); *C12N 2310/17* (2013.01); *C12N 2310/18* (2013.01); *A61K 31/7088* (2013.01); *A61K 45/06* (2013.01); *C12N 2310/315* (2013.01); *C12N 2310/151* (2013.01)
USPC ........................................ 514/44 A; 536/23.1

(58) Field of Classification Search
CPC .................. A61K 31/4164; A61K 2039/5152; A61K 2039/5156; A61K 2039/5154; A61K 31/7088; A61K 2300/00; A61K 45/06; C12N 5/0656; C12N 5/0617; C12N 15/117; C12N 2310/151; C12N 2310/315; C12N 2310/17; C12N 2310/18
USPC ........................................ 514/44 A; 536/23.1
See application file for complete search history.

(56) References Cited

U.S. PATENT DOCUMENTS

| | | |
|---|---|---|
| 4,469,863 A | 9/1984 | Ts'o et al. |
| 5,023,243 A | 6/1991 | Tullis |
| 5,663,153 A | 9/1997 | Hutcherson et al. |
| 6,207,646 B1 | 3/2001 | Krieg et al. |
| 6,214,806 B1 | 4/2001 | Krieg et al. |
| 6,699,493 B2 | 3/2004 | Wong |
| 7,094,766 B1 | 8/2006 | Gilchrest et al. |
| 7,244,710 B2* | 7/2007 | Catania et al. .................. 514/14 |
| 2003/0087848 A1 | 5/2003 | Bratzler et al. |
| 2003/0216431 A1* | 11/2003 | Raut ............................. 514/313 |
| 2004/0132682 A1 | 7/2004 | Klinman et al. |
| 2004/0248834 A1 | 12/2004 | Klinman et al. |
| 2006/0074039 A1 | 4/2006 | Klinman et al. |

FOREIGN PATENT DOCUMENTS

| | | |
|---|---|---|
| EP | 0 092 574 | 4/1992 |
| WO | WO 83/01451 | 4/1983 |
| WO | WO 95/26204 | 9/1995 |
| WO | WO 96/02555 | 2/1996 |
| WO | WO 98/11211 | 3/1998 |
| WO | WO 98/18810 | 5/1998 |
| WO | WO 98/30223 | 7/1998 |
| WO | WO 98/37919 | 9/1998 |
| WO | WO 98/40100 | 9/1998 |
| WO | WO 98/08861 | 10/1998 |
| WO | WO 98/45314 | 10/1998 |
| WO | WO 98/52581 | 11/1998 |
| WO | WO 99/51259 | 10/1999 |
| WO | WO 01/74342 | 10/2001 |
| WO | WO 03/027313 | 4/2003 |
| WO | WO 2004/012669 | 2/2004 |

OTHER PUBLICATIONS

Gursel et al J Immunol 2003; 171:1393-400.*
Zeuner et al Arthritis Rheum. 2002; 46(8):2219-24.*
Shirota et al J Immunol 2004; 173:5002-7.*
Ahuja et al Indian Journal of Ophthalmology, 1980, 28(4), 215-217.*
Lerner et al , Immune based disorders, in Current Clinical Neurology: Diagnostic criteria in Neurology, 127-146, 2003.*
Sakane et al N. Engl. J. Med. 341 (1999), pp. 1284-1291.*
McCluskie et al Mol. Med. 1999, 5:287-300.*
Afshari et al Curr Rheumatol Rep. 2001; 3(5):453-8.*
Baharav et al Drug Discovery Today: Disease Models, 2006, 3(1) 11-14.*
Hartmann et al., "Rational design of new CpG oligonucleotides that combine B cell activation with high IFN-α induction in plasmacytoid dendritic cells," *Eur. J. Immunol.* 33:1633-1641 (2003).
Shao et al., "CpG-Containing Oligodeoxynucleotide 1826 Converts the Weak Uveitogenic Rat Interphotoreceptor Retinoid-Binding Protein Peptide 1181-1191 into a Strong Uveitogen," *J. Immunology* 171:4780-4785 (2003).

(Continued)

*Primary Examiner* — Anoop Singh
(74) *Attorney, Agent, or Firm* — Klarquist Sparkman, LLP

(57) ABSTRACT

Pharmaceutical compositions are disclosed that are of use for the treatment of uveitis. These compositions include a suppressive oligonucleotide. These compositions including an immunosuppressive oligonucleotide can be used for the treatment of uveitis, including anterior, posterior, and diffuse uveitis.

17 Claims, 4 Drawing Sheets

(56) References Cited

OTHER PUBLICATIONS

Wasmuth et al., "Topical treatment with antisense oligonucleotides targeting tumor necrosis factor-alpha in herpetic stromal keratistis," *Investigative Ophthalmology & Visual Science* 44(12):5228-5234 (Dec. 2003).
Battegay, "Angiogenesis: mechanistic insights, neovascular diseases, and therapeutic prospects," *J. Mol. Med.* 73:333-346, 1995.
Beck and D'Amore, "Vascular development: cellular and molecular regulation," *FASEB J.* 11(5):365-373, 1997.
Bjersing et al., "Anti-proliferative effects of phosphodiester oligodeoxynucleotides," *Immunobiology*, 209(8):637-45, 2004.
Braun et al, "On the Difficulties of Establishing a conss3nsu on the D3efinition of and diagnostic Investigations for Reactive Arthritis. Results and discussion of a questionnaire prepared for the 4th International workshop on Reactive Arthritis, Berlin, Germany, Jul. 3-6, 1999,", *J. Rheumatol.* (2000) 27:2185-2192.
Britigan et al., "Lactoferrin Binds CpG-Containing Oligonucleotides and Inhibits Their Immunostimulatory Effects on Human B Cells," *J. Immunol.* 167:2921-2928, 2001.
Chatziantoniou, "Telomerase: Biological Function and Potential Role in Cancer Management," *Pathology Oncology Research* 7(3):161-170.
Chen et al., "Identification of methylated CpG motifs as inhibitors of the immune stimulatory CpG motifs," *Gene Ther.* 8(13):1024-1032, 2001.
Deng et al.,"Synovial cytokine mRNA expression during arthritis triggered by CpG motifs of bacterial DNA," *Arthritis Res*.3:48-53, 2001.
Deng et al., "The Features of Arthritis Induced by CPG Motifs in Bacterial DNA," *Arthritis Rheum.* 43:356-364, 2000.
Deng et al., "Intra-particularly localized bacterial DNA containing CPG motifs induces arthritis," 5(6):702-705, Jun. 1999.
Dong et al., "Suppressive Oligodeoxynucleotides Delay the Onset of Glomerulonephritis and Prolong Survival in Lupus-Prone NZB X NZW Mice," *Arthritis & Rheumatism* 52(2):651-658 (Feb. 2005).
Dong et al., "Suppressive Oligonucleotides Protect Against Collagen-Induced Arthritis in Mice," *Arthritis & Rheumatism* 50(5):1686-1689 (May 2004).
Enokizono et al., "Structure of hnRNP D Complexed with Single-stranded Telomere DNA and Unfolding of the Quadruplex by Heterogeneous Nuclear Ribonucleoprotein D," *J. Biological Chemistry* 280(19):18862-18870 (2005).
Gaudric et al,. "Quantification of Angiogenesis due to Basic Fibroblast Growth Factor in a Modified Rabbit Corneal Model," *Ophthal. Res.* 24: 181, 1992.
Gursel, I., et al., "Sterically Stabilized Cationic Liposomes Improve the Uptake and Immunostimulatory Activity of CpG Oligonucleotides," *J. Immunol.* 167: 3324, 2001.
Gursel, M., et al., "Differential and competitive activation of human immune cells by distinct classes of CpG oligodeoxynucleotide," *J.Leuko.Biol.* 71:813-820, 2002.
Gursel et al., "Repetitive Elements in Mammalian Telomeres Suppress Bacterial DNA-Induced Immune Activation," *J. Immunology* 171:1393-1400 (2003).
Han & Hurley, "G-quadruplex DNA: a potential target for anti-cancer drug design," *Trends Pharmacol. Sci.* 21:136-142, 2000.
Hartmann et al., "CpG DNA: A potent signal for growth, activation, and maturation of human dendritic cells," *Proc. Natl. Acad. Sci. USA* 96:9305-9310, 1999.
Ho et al., "An Immunomodulatory GpG Oligonucleotide for the Treatment of Autoimmunity via the Innate and Adaptive Immune Systems," *J. Immunol.* 171:4920-4926, 2003.
Iwakura et al., "The Development of Autoimmune Inflammatory Arthropathy in Mice Transgenic for the Human T Cell Leukemia Virus Type-1 env-pX Region is not Dependent on H-2 Haplotypes and Modified by the Expression Levels of Fas Antigen," *J. Immunology* 161:6592-6598, 1998.
Kenyon et al., "A Model of Angiogenesis in the Mouse Cornea," *Invest Opthalmol. Vis. Sci.* 37:1625-1632, 1996.

Klinman et al., "CpG motifs present in bacterial DNA rapidly induce lymphocytes to secrete interleukin 6, interleukin 12, and interferon y," *Proc. Natl. Acad. Sci.* USA 93: 2879, 1996.
Klinman, D. M., et al., "Contribution of CpG Motifs to the Immunogenicity of DNA Vaccines," *J. Immunol.* 158:3635-3639, 1997.
Klinman et al., "Activation of the innate immune system by CpG oligonucleotides: immunoprotective activity and safety," *Springer Semin. Immunopathol.* (2000) 22:173-83.
Krieg et al., "CpG motifs in bacterial DNA trigger direct B-cell activation," *Nature* 374: 546, 1995.
Krieg et al., "Sequence motifs in adenoviral DNA block immune activation by stimulatory CpG motifs," *Proc. Natl. Acad. Sci. USA* 95:12631-12636, 1998.
Krieg, "Commentary: A possible cause of joint destruction in septic arthritis," *Arthritis Research* 1(1):3-4, 1999.
Krieg, "From bugs to drugs: therapeutic immunomodulation with oligodeoxynucleotides containing CpG sequences from bacterial DNA," *Antisense Nucleic Acid Drug Dev* 11(3):181-188; 2001.
Krieg et al., "Enhancing vaccines with immune stimulatory CpG DNA," *Curr Opin Mol Ther* 3(1):15-24, 2001.
Krieg, "From A to Z on CpG," *Trends Immunol.* 23(2):64-65, 20002.
Krieg, "CpG Motifs in bacterial DNA and their immune effects," *Annu Rev Immunol* 20:709-760, 2002.
Liang et al., "Activation of Human B Cells by Phosphorothioate Oligodeoxynucleotides," *J. Clin. Invest.* 98:1119, 1996.
Lichtenberg et al., "The Rat Subcutaneous Air Sac Model: A Quantitative Assay of Antiangiogenesis in Induced Vessels," *Pharmacol Toxicol.* 84: 34, 1999.
Murchie & Lilley, "Tetraplex folding of telomere sequences and the inclusion of adenine bases," *EMBO J.* 13:993-1001, 1994.
Pisetsky et al., "Immunological Properties of Bacterial DNA," *NY Acad Sci.* 772:152-163, 1995.
Pisetsky et al., "Inihibition of Murine Macrophage IL-12 Production by Natural and Synthetic DNA," *Clin. Immunol.* 96, 198-204, 2000.
Quarcoo et al., "Inhibition of signal transducer and activator of transcription 1 attenuates allergen-induced airway inflammation and hyperreactivity," *J Allergy Clin Immunol.*, 114(2):288-95, 2004.
Roman, M., et al., "Immunostimulatory DNA sequences function as T helper-1-promoting adjuvants," *Nature Medicine* (1997) 3:849.
Schwartz et al., CpG Motifs in Bacterial DNA Cause Inflammation in the Lower Respiratory Tract, *J. Clin. Invest.* 100:68-73, 1997.
Schwartz et al., "Bacterial DNA or Oligonucleotides Containing Unmethylated CpG Motifs Can Minimize Lipopolysaccharide-Induced Inflammation in the Lower Respiratory Tract Through an IL-12-Dependent Pathway," *J. Immunol.* 163:224-231, 1999.
Shirota et al., "Suppressive Oligodeoxynucleotides Protect Mice from Lethal Endotoxic Shock," *J. Immunology* 174:4579-4583 (2005).
Stunz et al., "Inhibitory oligonucleotides specifically block effects of stimulatory CpG oligonucleotides in B cells," *Eur. J. Immunol.* 32:1212-1222, 2002.
Verthelyi et al., "Human Peripheral Blood Cells Differentially Recognize and Respond to Two Distinct CpG Motifs," *J. Immunol.* 166:2372-2377, 2001.
Vialas et al., "Oxidative Damage Generated by an Oxo-Metalloporophyrin onto the Human Telomeric Sequence," *Biochemistry* 39:9514-9522, 2000.
Wilting et al., "A modified chorioallantoic membrane (CAM) assay for qualitative and quantitative study of growth factors," *Anat. Embryol.* 183: 259, 1991.
Yamada et al., "Effect of suppressive DNA on CpG-Induced Immune Activation," *J. Immunol.* 169:5590-5594, 2002.
Yamamoto et al., "Unique Palindromic Sequences in Synthetic Oligonucleotides are Required to Induce INF and Augment INF-Mediated Natural Killer," *J. Immunol.* 148:4072, 1992.
Yi et al., "Rapid Immune Activation by CpG Motifs in Bacterial DNA," *J. Immun.* 157:5394, 1996.
Zeuner et al., "Reduction of CpG-Induced Arthritis by Suppressive Oligonucleotides," *Arthritis & Rheumatism* 46(8):2219-2224, 2002.
Zheng et al., "DNA containing CpG motifs induces angiogenesis," *PNAS* 99(13):8944-8949, 2002.

(56) References Cited

OTHER PUBLICATIONS

Zhao et al., "Requirements for effective inhibition of immunostimulatory CpG motifs by neutralizing motifs." *Antisense Nucleic Acid Drug Dev.* 10(5):381-389, 2000.

Kotake, S., "Is the Era of Tailor-Made Treatment for Uveitis at Hand?" *Advanced Treatments for Ophthalmologists, No. 13, New Ophthalmology* 19(N1):p. 81-82 (2002) (in Japanese, with accompanying English language translation).

Chatziantoniou, "Telomerase: Biological Function and Potential Role in Cancer Management," *Pathology Oncology Research* 7(3):161-170, 2001.

\* cited by examiner

SEQUENCE LISTING

```
<160> NUMBER OF SEQ ID NOS: 25

<210> SEQ ID NO 1
<211> LENGTH: 16
<212> TYPE: DNA
<213> ORGANISM: Artificial Sequence
<220> FEATURE:
<223> OTHER INFORMATION: oligodeoxynucleotide

<400> SEQUENCE: 1
cctcaagctt gagggg                                                      16

<210> SEQ ID NO 2
<211> LENGTH: 24
<212> TYPE: DNA
<213> ORGANISM: Artificial Sequence
<220> FEATURE:
<223> OTHER INFORMATION: oligodeoxynucleotide

<400> SEQUENCE: 2
ttagggttag ggttagggtt aggg                                             24

<210> SEQ ID NO 3
<211> LENGTH: 18
<212> TYPE: DNA
<213> ORGANISM: Artificial Sequence
<220> FEATURE:
<223> OTHER INFORMATION: oligodeoxynucleotide

<400> SEQUENCE: 3
ttagggttag ggttaggg                                                    18

<210> SEQ ID NO 4
<211> LENGTH: 12
<212> TYPE: DNA
<213> ORGANISM: Artificial Sequence
<220> FEATURE:
<223> OTHER INFORMATION: oligodeoxynucleotide
```

```
<400> SEQUENCE: 4
ttagggttag gg                                                    12

<210> SEQ ID NO 5
<211> LENGTH: 24
<212> TYPE: DNA
<213> ORGANISM: Artificial Sequence
<220> FEATURE:
<223> OTHER INFORMATION: Oligodeoxynucleotide

<400> SEQUENCE: 5
tgggcggttg ggcggttggg cggt                                       24

<210> SEQ ID NO 6
<211> LENGTH: 16
<212> TYPE: DNA
<213> ORGANISM: Artificial Sequence
<220> FEATURE:
<223> OTHER INFORMATION: Oligodeoxynucleotide

<400> SEQUENCE: 6
tgggcggttg ggcggt                                                16

<210> SEQ ID NO 7
<211> LENGTH: 16
<212> TYPE: DNA
<213> ORGANISM: Artificial Sequence
<220> FEATURE:
<223> OTHER INFORMATION: Oligodeoxynucleotide

<400> SEQUENCE: 7
tcaaccttca ttaggg                                                16

<210> SEQ ID NO 8
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 8
ttagggttag ggtcaacctt ca                                         22

<210> SEQ ID NO 9
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 9
tcaaccttca ttagggttag gg                                         22

<210> SEQ ID NO 10
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 10
gggttagggt tatcaacctt ca                                         22

<210> SEQ ID NO 11
```

```
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 11
tcaaccttca gggttagggt ta                                              22

<210> SEQ ID NO 12
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 12
gggtgggtgg gtattaccat ta                                              22

<210> SEQ ID NO 13
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 13
attaccatta gggtgggtgg gt                                              22

<210> SEQ ID NO 14
<211> LENGTH: 18
<212> TYPE: DNA
<213> ORGANISM: Artificial Sequence
<220> FEATURE:
<223> OTHER INFORMATION: Oligodeoxynucleotide

<400> SEQUENCE: 14
tgggcggttc aagcttga                                                   18

<210> SEQ ID NO 15
<211> LENGTH: 18
<212> TYPE: DNA
<213> ORGANISM: Artificial Sequence
<220> FEATURE:
<223> OTHER INFORMATION: Oligodeoxynucleotide

<400> SEQUENCE: 15
tcaagcttca tgggcggt                                                   18

<210> SEQ ID NO 16
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 16
gggtgggtgg gtagacgtta cc                                              22

<210> SEQ ID NO 17
<211> LENGTH: 16
<212> TYPE: DNA
<213> ORGANISM: Artificial Sequence
<220> FEATURE:
<223> OTHER INFORMATION: Oligodeoxynucleotide

<400> SEQUENCE: 17
```

```
gggggtcaa gcttca                                          16

<210> SEQ ID NO 18
<211> LENGTH: 16
<212> TYPE: DNA
<213> ORGANISM: Artificial Sequence
<220> FEATURE:
<223> OTHER INFORMATION: Oligodeoxynucleotide

<400> SEQUENCE: 18
tcaagcttca gggggg                                         16

<210> SEQ ID NO 19
<211> LENGTH: 16
<212> TYPE: DNA
<213> ORGANISM: Artificial Sequence
<220> FEATURE:
<223> OTHER INFORMATION: Oligodeoxynucleotide

<400> SEQUENCE: 19 gggggtcaa cgttca                                          16

<210> SEQ ID NO 20
<211> LENGTH: 20
<212> TYPE: DNA
<213> ORGANISM: Artificial Sequence
<220> FEATURE:
<223> OTHER INFORMATION: Oligodeoxynucleotide

<400> SEQUENCE: 20
gagcaagctg gaccttccat                                     20

<210> SEQ ID NO 21
<211> LENGTH: 21
<212> TYPE: DNA
<213> ORGANISM: Artificial Sequence
<220> FEATURE:
<223> OTHER INFORMATION: Oligodeoxynucleotide

<400> SEQUENCE: 21
gagcaagctg gtagacgtta g                                   21

<210> SEQ ID NO 22
<211> LENGTH: 20
<212> TYPE: DNA
<213> ORGANISM: Artificial Sequence
<220> FEATURE:
<223> OTHER INFORMATION: Oligodeoxynucleotide

<400> SEQUENCE: 22
gggcaagctg gacctggggg                                     20

<210> SEQ ID NO 23
<211> LENGTH: 20
<212> TYPE: DNA
<213> ORGANISM: Artificial Sequence
<220> FEATURE:
<223> OTHER INFORMATION: Oligodeoxynucleotide

<400> SEQUENCE: 23
ggggaagctg gacctggggg                                     20

<210> SEQ ID NO 24
<211> LENGTH: 20
<212> TYPE: DNA
```

```
<213> ORGANISM: Artificial Sequence
<220> FEATURE:
<223> OTHER INFORMATION: Oligodeoxynucleotide

<400> SEQUENCE: 24
gggcaagctg gaccttcggg                                              20

<210> SEQ ID NO 25
<211> LENGTH: 22
<212> TYPE: DNA
<213> ORGANISM: Artificial Sequence
<220> FEATURE:
<223> OTHER INFORMATION: Oligodeoxynucleotide

<400> SEQUENCE: 25
ggcaagctgg accttcgggg gg                                           22
```

METHODS AND COMPOSITIONS FOR THE TREATMENT OF UVEITIS

CROSS-REFERENCE TO RELATED APPLICATIONS

This is the U.S. National Stage of International Application No. PCT/US2005/015761, filed May 5, 2005, which was published in English under PCT Article 21(2), which in turn claims the benefit of U.S. Provisional Application No. 60/569,276, filed May 6, 2004, which is incorporated herein by reference in its entirety.

FIELD

This relates to field of pharmaceutical compositions for the treatment of uveitis.

BACKGROUND

Intraocular inflammatory diseases grouped under the term "uveitis" are a major cause of visual loss in industrialized nations. "Uveitis" refers to an intraocular inflammation of the uveal tract, namely, the iris, choroids, and ciliary body. Uveitis is responsible for about 10% of legal blindness in the United States (National Institutes of Health, *Interim Report of the Advisory Eye Council Support for Visual Research*, U.S. Department of Health Education and Welfare, Washington, D.C., 1976, pp. 20-22). Complications associated with uveitis include posterior synechia, cataract, glaucoma and retinal edema (Smith et al., *Immunol. Cell Biol.* 76:497-512, 1998).

Treatment of uveitis often focuses on the control the inflammatory symptoms. In such cases, corticosteroids are often used to suppress inflammation in the eye. Anterior uveitis often responds to local steroid treatment with eye drops. However, drops do not usually provide therapeutic levels of steroids in the posterior part of the eye for the treatment of posterior uveitis or panuveitis. Periocular injections are then indicated. These injections can be given sub-conjunctivally or beneath Tenon's capsule.

Systemic treatments with corticosteroids are often used when local injections fail. However, many of the most severe cases of uveitis do not respond to high dose systemic corticosteroid therapy. In addition, the side effects of such systemic therapies can include hypertension, hyperglycemia, peptic ulceration, Cushingoid features, osteoporosis, growth limitation, myopathy, psychosis and increased susceptibility to infection can be devastating. Finally, many of the local and systemic steroid therapies also have potentially sight-threatening side effects such as glaucoma, cataract and susceptibility to eye infection. Newer immunosuppressive agents are being investigated for use in uveitis treatment, such as Tacrolimus, Sirolimus and mycophelonate mofetil. However, these drugs also have serious side effects (Anglade and Whitcup, *Drugs* 49:213-223, 1995). Therefore, there exists a need for new methods to treat inflammatory disease of the eye.

SUMMARY

Pharmaceutical compositions are disclosed that are of use for the treatment of intraocular inflammation, such as uveitis. These compositions include a therapeutically effective amount of a suppressive oligonucleotide. These compositions can be used for the treatment of uveitis, including anterior, posterior and diffuse uveitis.

The foregoing and other features and advantages will become more apparent from the following detailed description of several embodiments, which proceeds with reference to the accompanying figures.

BRIEF DESCRIPTION OF THE FIGURES

FIG. 1A is a diagram of the structure of an individual G-tetrad that shows the Hoogsteen base pairing. $M^+$ represents a monovalent cation such as $K^+$ or $Na^+$, and dR is the sugar-phosphate backbone. FIG. 1B is a schematic representation showing the possible folded intramolecular quadruplex structure. FIG. 1C is a schematic diagram showing the GG-base pair formed by means of Hoogsteen hydrogen bonds. FIG. 1D is a schematic diagram of an intramolecular hairpin.

FIG. 6A is a plot of the histology scores obtained when transgenic mice expressing hen egg lysozyme (HEL) in their lens (under control of the alphaA crystallin promoter) are injected with $0.35 \times 10^6$ T-helper type 1 lymphocytes specific against HEL. FIG. 6B is a plot of the histology scores obtained when transgenic mice expressing hen egg lysozyme (HEL) in their lens (under control of the alphaA crystallin promoter) are injected with 0.20×10⁶ T-helper type 1 lymphocytes specific against HEL.

SEQUENCE LISTING

Figure 1:
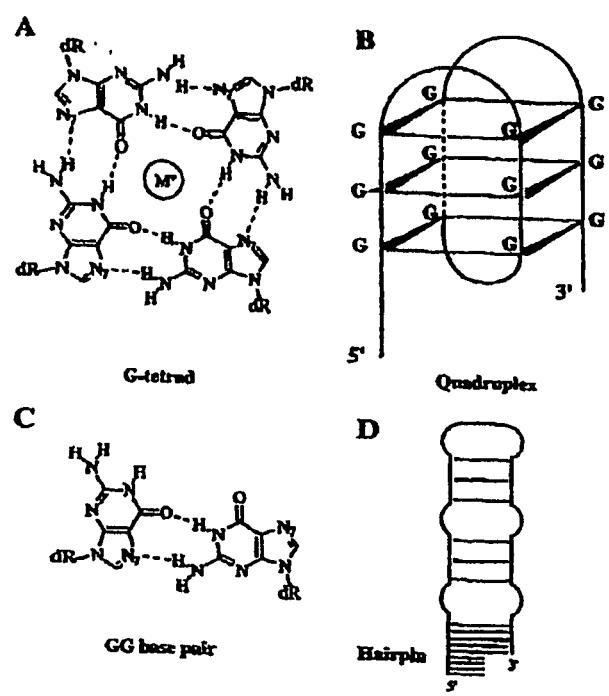
FIG. 1 is a set of diagrams of the structure of a G-tetrad.

The nucleic and amino acid sequences listed in the accompanying sequence listing are shown using standard letter abbreviations for nucleotide bases, and three letter code for amino acids, as defined in 37 C.F.R. 1.822.

SEQ ID NOs: 1-25 are the nucleic acid sequences of suppressive oligonucleotides. It should be noted that SEQ ID NO: 2 is the nucleic acid sequence of A151.

SEQ ID NO: 26 is the nucleic acid sequence of a control ODN.

DETAILED DESCRIPTION

I. Abbreviations

CFA: complete Freund's adjuvant
EAU: experimental autoimmune uveitis
ELISA: enzyme linked immunosorbant assay
HEL: hen egg lysozyme
Hrs: hours
IFN-g: interferon gamma
IL4: interleukin 4
i.p.: intraperitoneally
IRBP: interphotoreceptor retinoid-binding protein
ODN: oligonucleotide
PPD: purified protein derivative
PBS: phosphate buffered saline
S-Ag: S-antigen or arrestin
μg: microgram

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided.

Animal: Living multi-cellular vertebrate organisms, a category that includes, for example, mammals and birds. The term mammal includes both human and non-human mammals. Similarly, the term "subject" includes both human and veterinary subjects.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. An "epitope" is one or more particular chemical groups or peptide sequences on a molecule that are antigenic (that elicit a specific immune response). An antibody binds a particular antigenic epitope.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target. In one embodiment, an antisense molecule specifically hybridizes to a target mRNA and inhibits transcription of the target mRNA.

Autoimmune disorder: A disorder in which the immune system produces an immune response (e.g., a B cell or a T cell response) against an endogenous antigen, with consequent injury to tissues. For example, rheumatoid arthritis is an autoimmune disorder, as are Hashimoto's thyroiditis, pernicious anemia, Addison's disease, type I diabetes, Sjogren's syndrome, dermatomyositis, lupus erythematosus, multiple sclerosis, myasthenia gravis, Reiter's syndrome, and Grave's disease, among others.

Circular Dicromism (CD) value: The formation of G-tetrads yields a complex with different physical properties than the individual oligonucleotides. Spectroscopically, this is manifested by an increase in circular dicroism (CD), and an increase in peak absorbance to the 260-280 nm wavelength owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. The higher the ellipticity value the greater the tetrad-forming capacity of the oligonucleotide.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A "CpG oligonucleotide" or an "immunostimulatory CpG oligonucleotide" is an oligonucleotide that is at least about ten nucleotides in length and includes an unmethylated CpG motif. CpG oligonucleotides include both D and K type oligodeoxynucleotides (see Verthelyi et al., *J Immunol.* 166:2372-2377, 2001, which is herein incorporated by reference). CpG oligonucleotides also include C type oligodeoxynucleotides (see Hartmann et al., *Eur. J Immunol.* 33:1633-1641, 2003, herein incorporated by reference), which activate B cells and dendritic cells. CpG oligodeoxynucleotides are single-stranded. The entire CpG oligodeoxynucleotide can be unmethylated or portions may be unmethylated. In one embodiment, at least the C of the 5' CG 3' is unmethylated.

Cytokine: Proteins made by cells that affect the behavior of other cells, such as lymphocytes. In one embodiment, a cytokine is a chemokine, a molecule that affects cellular trafficking. In another embodiment, a cytokine alters the maturation of lymphocytes, and influences isotype switching by B cells.

Experimental Autoimmune Uveoretinitis (EAU): An animal model for uveitis that can be induced by several retinal autoantigens (see Gery and Streilein, *Curr. Opinion Immunol.* 6:938, 1994; Nussenblatt and Gery, *J. Autoimmunity* 9:575-585, 1996; Gery et al., "Autoimmune Diseases of the Eye. In: Theofilopoulos and Bona" (eds.), The *Molecular Pathology of Autoimmune Diseases*, 2nd Edition, Taylor and Francis, New York, pp. 978-998, 2002). Generally, intraocular inflammation is induced in a non-human animal species using an autoantigen. For example, immunization of a mouse, rat, rabbit or pig with an ocular-specific antigen can be used to produce the model system. Both arrestin and interphotoreceptor retinol protein (IRBP, for amino acid sequences see Swissprot Accession Nos. P12661, P49194, P12662) have been used to produce EAU.

Experimental autoimmune uveoretinitis (EAU) can be induced by several autoantigens derived from the retina One of the most evaluated antigen and model systems is EAU induced by the retinal S-antigen (S-Ag, see Swissprot Accession Nos. Q99858, P10523, P20443, P36576). S-Ag binds phosphorylated cytopigments and blocks the interaction of transducin with the photoexcited light receptor of the visual cascade. S-Ag is the only retinal autoantigen to which a substantial number of human patients with endogenous intermediate and posterior uveitis consistently demonstrate in vitro proliferative responses (Nussenblaft et al., *Am. J. Ophthalmol.* 89:173, 1980; Nussenblatt et al., *Am. J Ophthalmol.* 94:147, 1982). The entire amino acid sequence of S-Ag has been described, with two fragments designated N and M, respectively, demonstrating uveitogenicity (Donoso et al., *Curr. Eye Res.* 8:1151, 1987; Singh et al., *Cell. Immunol.* 115:413, 1988). Immune manipulation of this model appears to have excellent predictive value for the human uveoretinitis, as was demonstrated with the clinical effectiveness of cyclosporine use in humans (Nussenblatt et al., *J. Clin. Invest.* 67:1228, 1981) which was first tested on the EAU model.

Functionally Equivalent: Sequence alterations, for example in a suppressive ODN, that yield the same results as described herein. Such sequence alterations can include, but are not limited to, deletions, base modifications, mutations, labeling, and insertions.

G-tetrad: G-tetrads are G-rich DNA segments that can accommodate complex secondary and/or tertiary structures (see FIG. 1). A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of contiguous Gs, and the higher the G content of the ODN, the higher the likelihood of G-tetrad formation, as reflected by higher CD or ellipticity values.

Oligonucleotides that form G-tetrads can also form higher-level aggregates that are more easily recognized and taken up by immune cells, for example, through scavenger receptors or by nucleolin.

Guanosine-rich sequence: A hexameric region of a nucleotide sequence in which >50% of the bases are Gs.

Immunosuppressive agent: A molecule, such as a chemical compound, small molecule, steroid, nucleic acid molecule, or other biological agent, that can decrease an immune response such as an inflammatory reaction. Immunosuppressive agents include, but are not limited to an agent of use in treating uveitis. Specific, non-limiting examples of immunosuppressive agents are corticosteroids, cyclosporine A, FK506, and anti-CD4. In additional examples, the agent is a biological response modifier, such as Kineret® (anakinra), Enbrel® (etanercept), or Remicade® (infliximab), a disease-modifying antirheumatic drug (DMARD), such as Arava® (leflunomide). Agents of use to treat inflammation include non-steroidal anti-inflammatory drugs (NSAIDs), specifically a Cyclo-Oxygenase-2 (COX-2) inhibitor, such as Celebrex® (celecoxib) and Vioxx® (rofecoxib), or another product, such as Hyalgan® (hyaluronan) and Synvisc® (hylan G-F20). Additional immunosuppressive agents are disclosed herein.

Immune-mediated disorder: A disorder that involves an unwanted immune response. Although immune recognition of "non-self" proteins is essential to avoid and eliminate infection, the immune response can sometimes be unwanted. The disorder can be an autoimmune disorder, an inflammatory disorder, graft versus host disease, rejection of a transplanted heterologous tissue, or an allergic disorder.

Immune response: A response of a cell of the immune system, such as a B cell, T cell, or macrophage, to a stimulus. In one embodiment, the response is specific for a particular antigen (an "antigen-specific response").

Inflammation: A series of local tissue reactions that take place at a site of injury and have an immunological component. The injury may be due to trauma, lack of blood supply, hemorrhage, autoimmune attack, transplanted exogenous tissue or infection. This generalized response by the body includes the release of many components of the immune system (such as cytokines), attraction of cells to the site of the damage, swelling of tissue due to the release of fluid and other processes. Inflammation can be of an infectious or a non-infectious etiology. In the eye, inflammation produces vascular dilation, fluid leakage into extra-vascular spaces, migration of leukocytes and other cells.

Infectious agent: An agent that can infect a subject, including, but not limited to, viruses, bacteria and fungi.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids and proteins.

Leukocyte: Cells in the blood, also termed "white cells," that are involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Nucleic acid: A deoxyribonucleotide or ribonucleotide polymer in either single- or double-stranded form, and unless otherwise limited, encompasses known analogs of natural nucleotides that hybridize to nucleic acids in a manner similar to naturally occurring nucleotides.

Oligonucleotide or "oligo": Multiple nucleotides (i.e., molecules comprising a sugar (e.g., ribose or deoxyribose) linked to a phosphate group and to an exchangeable organic base, which is either a substituted pyrimidine (Py) (e.g., cytosine (C), thymine (T) or uracil (U)) or a substituted purine (Pu) (e.g., adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e., an oligonucleotide minus the phosphate) and any other organic base polymer. Oligonucleotides can be obtained from existing nucleic acid sources (e.g., genomic or cDNA), but are preferably synthetic (e.g., produced by oligonucleotide synthesis).

A "stabilized ODN" is an ODN that is relatively resistant to in vivo degradation (for example via an exo- or endo-nuclease). In one embodiment, a stabilized ODN has a modified phosphate backbone. One specific, non-limiting example of a stabilized ODN has a phosphorothioate modified phosphate backbone (wherein at least one of the phosphate oxygens is replaced by sulfur). Other stabilized ODNs include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. ODNs which contain a diol, such as tetraethyleneglycol or hexaethyleneglycol, at either or both termini have also been shown to be substantially resistant to nuclease degradation.

An "immunostimulatory ODN," "immunostimulatory CpG containing ODN," "CpG ODN," refers to an oligodeoxynucleotide, which contains a cytosine, guanine dinucleotide sequence and stimulates (e.g., has a mitogenic effect) vertebrate immune cells. The cytosine, guanine is unmethylated. Immunostimulatory oligonucleotides include those oligonucleotides that are at least about ten nucleotides in length and have an unmethylated CpG motif in their nucleic acid sequence. D and K type oligodeoxynucleotides (see Verthelyi et al., *J. Immunol.* 166:2372-2377, 2001, which is herein incorporated by reference) and C type oligodeoxynucleotides (see Hartmann et al., *Eur. J Immunol.* 33:1633-1641, 2003, herein incorporated by reference) are immunostimulatory ODNs.

A "suppressive ODN" refers to an oligonucleotide capable of reducing an immune response, such as inflammation. These ODNs are described in detail herein. Suppressive ODNs are DNA molecules of at least eight nucleotides in length, wherein the ODN forms a G-tetrad, and has a CD value of greater than about 2.9. In a suppressive ODN, the number of guanosines is at least two. In one embodiment, a suppressive ODN inhibits immune activation caused by CpG DNA when administered prior to, concurrently with, or after the administration of a CpG ODN.

An "ODN delivery complex" is an ODN associated with (for example, ionically or covalently bound to; or encapsulated within) a targeting means (e.g., a molecule that results in a higher affinity binding to a target cell (for example, B cell or natural killer (NK) cell) surface and/or increased cellular uptake by target cells). Examples of ODN delivery complexes include ODNs associated with: a sterol (for example, cholesterol), a lipid (for example, cationic lipid, virosome or liposome), or a target cell specific binding agent (for example, a ligand recognized by a target cell specific receptor). Generally, complexes are sufficiently stable in vivo to prevent significant uncoupling prior to internalization by the target cell. However, the complex can be cleavable or otherwise accessible under appropriate conditions within the cell so that the oligonucleotide is functional. (Gursel, *J. Immunol.* 167:3324, 2001).

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, intra-vitreously, or subcutaneously, and various surface applications including intranasal, intradermal, and topical application, for instance.

Pharmaceutical agent or drug: A chemical compound or composition capable of inducing a desired therapeutic or prophylactic effect when properly administered to a subject. Pharmaceutical agents include, but are not limited to, chemotherapeutic agents and anti-infective agents.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: "Preventing" a disease refers to inhibiting the full development of a disease, for example in a person who is known to have a predisposition to a disease such as an autoimmune disorder. An example of a person with a known predisposition is someone with a history of a disease in the family, or who has been exposed to factors that predispose the subject to a condition. "Treatment" refers to a therapeutic intervention that ameliorates a sign or symptom of a disease or pathological condition after it has begun to develop.

Purified: The term purified does not require absolute purity, rather, it is intended as a relative term. Thus, for example, a purified peptide or nucleic acid preparation is one in which the peptide, protein or nucleic acid is more enriched than the peptide, protein or nucleic acid is in its natural environment within a cell. Preferably, a preparation is purified such that the protein, peptide or nucleic acid represents at least 50% of the total peptide, protein or nucleic acid content of the preparation, such as is at least about 80%, 905, 95%, 98%, 990/o or 100% of the content.

Therapeutic agent: Used in a generic sense, it includes treating agents, prophylactic agents, and replacement agents. A suppressive ODN is one form of a therapeutic agent.

Therapeutically effective amount: A quantity of an agent sufficient to achieve a desired effect in a subject being treated. For instance, this can be the amount of a suppressive ODN necessary to suppress CpG-induced immune cell activation in a subject, or a dose sufficient to prevent advancement, or to cause regression of a disease, such as uveitis, or which is capable of relieving symptoms caused by a disease, such as ocular inflammation. In one example, the amount is sufficient to prevent advancement, or to cause regression of the disease. In another example, the amount is sufficient to inhibit a sign or symptom of uveitis, such as the presence of inflammatory cells in the anterior chamber of the eye or spasm of the ciliary body, or to reduce lymphocyte infiltration.

An effective amount of a suppressive ODN can be administered systemically or locally (see below). In addition, an effective amount of a suppressive ODN can be administered in a single dose, or in several doses, for example daily, during a course of treatment. However, the effective amount of the ODN will be dependent on the preparation applied, the subject being treated, the severity and type of the affliction, and the manner of administration of the compound. For example, a therapeutically effective amount of a suppressive ODN can vary from about 0.01 mg/kg body weight to about 1 g/kg body weight in some embodiments, or from about 0.01 mg/kg to about 60 mg/kg of body weight, based on efficacy.

The suppressive ODNs disclosed herein have equal applications in medical and veterinary settings. Therefore, the general terms "subject" and "subject being treated" are understood to include all animals, including humans or other simians, dogs, cats, horses, and cows.

Uveal tract: The uveal tract is composed of three parts, the iris, the ciliary body, and the choroid. It is the middle, vascular layer of the eye, protected externally by the cornea and the sclera. It contributes to the blood supply of the retina.

The iris is the anterior section of the ciliary body. It has a relatively flat surface with an aperture in the middle called the pupil. The iris lies in contact with the lens and divides the anterior chamber from the posterior chamber. The function of the iris is to control the amount of light that enters the eye.

The ciliary body extends forward from the anterior termination of the choroid to the root of the iris. It is composed of two zones, the pars plicata and the pars plana. There are two layers of epithelium in the ciliary body, the external pigmented and an internal non-pigmented layer. The ciliary body forms the root of the iris and governs the size of the lens. Aqueous humor is secreted by the ciliary processes into the posterior chamber of the eye.

The choroid is the posterior portion of the uveal tract and the middle part of the eye, which lies between the retina and the sclera. It is largely composed of blood vessels. The function of the choroid is to nourish the outer portion of the underlying retina.

Uveitus: An intraocular inflammatory disease that includes iritis, cyclitis, panuveits, posterior uveitis and anterior uveitis. Iritis is inflammation of the iris. Cyclitis is inflammation of the ciliary body. Panuveitis refers to inflammation of the entire uveal (vascular) layer of the eye. Intermediate uveitis, also called peripheral uveitis, is centered in the area immediately behind the iris and lens in the region of the ciliary body and pars plana, and is also termed "cyclitis" and "pars planitis."

"Posterior" uveitis generally refers to chorioretinitis (inflammation of the choroid and retina). Posterior uveitis can give rise to diverse symptoms but most commonly causes floaters and decreased vision similar to intermediate uveitis. Signs include cells in the vitreous humor, white or yellow-white lesions in the retina and/or underlying choroid, exudative retinal detachments, retinal vasculitis, and optic nerve edema.

Anterior uveitis refers to iridocyclitis (inflammation of the iris and the ciliary body) and/or iritis. Anterior uveitis tends to be the most symptomatic, typically presenting with pain, redness, photophobia, and decreased vision. Signs of anterior uveitis include pupillary miosis and injections of the conjunctiva adjacent to the cornea, so-called perilimbal flush. Biomicroscopic, or slit lamp, findings include cells and flare in the aqueous humor as well as keratic precipitates, which are clumps of cells and proteinaceous material adherent to the corneal endothelium. "Diffuse" uveitis implies inflammation involving all parts of the eye, including anterior, intermediate, and posterior structures.

"Acute" uveitis is a form of uveitis in which signs and symptoms occur suddenly and last for up to about six weeks. "Chronic" uveitis is a form in which onset is gradual and lasts longer than about six weeks.

The inflammatory products (i.e., cells, fibrin, excess proteins) of ocular inflammation are commonly found in the fluid spaces of the eye, i.e., anterior chamber, posterior chamber and vitreous space as well as infiltrating the tissue imminently involved in the inflammatory response.

Uveitis may occur following surgical or traumatic injury to the eye; as a component of an autoimmune disorder (such as rheumatoid arthritis, Bechet's disease, ankylosing spondylitis, sarcoidosis), as an isolated immune mediated ocular disorder (such as pars planitis or iridocyclitis), as a disease unassociated with known etiologies, and following certain systemic diseases which cause antibody-antigen complexes to be deposited in the uveal tissues. Uveitis includes ocular inflammation associated with Bechet's disease, sarcoidosis, Vogt-Koyanagi-Harada syndrome, birdshot chorioretinopathy and sympathetic ophthalmia. Thus, non-infectious uveitis occurs in the absence of an infectious agent.

A wide variety of infective agents can also cause uveitis. When an infective etiology has been diagnosed, an appropriate antimicrobial drug can be given to cure the disease. However, the etiology of uveitis remains elusive in the majority of cases.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

A. Suppressive Oligodeoxynucleotides and Guanosine-Quadruplexes (G-Tetrads)

The present disclosure relates to a class of DNA motifs that selectively inhibits or suppresses immune activation. These ODN are described in PCT Application No. PCT/US02/30532, which is herein incorporated by reference. Optimal activity is observed using multimers of these motifs, which are rich in G bases and capable of forming G-quadruplexes (G-tetrads). G-tetrads are G-rich DNA segments that can accommodate complex secondary and/or tertiary structures (see FIG. 1). The suppressive ODNs of the disclosure are highly specific (i.e., are neither toxic nor non-specifically immunosuppressive), and are useful for inhibiting an immune response. In one embodiment, a suppressive ODN is of use for blocking immunostimulation caused by CpG motifs in vivo and in vitro.

A G-tetrad involves the planar association of four Gs in a cyclic Hoogsteen hydrogen bonding arrangement (this involves non-Watson Crick base-pairing). In general, either a run of two or more contiguous Gs or a hexameric region in which >50% of the bases are Gs, is needed for an ODN to form a G-tetrad. The longer the run of continuous Gs, and the higher the G content of the ODN, the higher the likelihood of G-tetrad formation, as reflected by higher ellipticity values. Oligonucleotides that form G-tetrads can also form higher-level aggregates that are more easily recognized and taken up by immune cells, for example, through scavenger receptors or by nucleolin.

The formation of G-tetrads yields a complex with different physical properties than the individual oligonucleotides. Spectroscopically, this is manifested by an increase in circular dicroism (CD), and an increase in peak absorbance to the 260-280 nm wavelength owing to the formation of secondary structures. Thus, a convenient method for identifying oligonucleotides that form G-tetrads is to study their CD values. An increase in peak ellipticity values to greater than 2.0 is typical of a G-tetrad forming oligonucleotide. For instance, G-tetrad-forming ODNs can have CD values of 2.2, 2.4, 2.6, 2.8, 3.0, 3.2, 3.5, 4.0, 4.5, 5.0, 5.5, 6.0, 6.5, 7.0, 7.5, 8.0, 8.5, 9.0, or higher. The higher the ellipticity value, the greater the tetrad-forming capacity of the oligonucleotide, so an ODN with a CD value of 8.5 is typically more suppressive than an ODN with a CD value of 2.9.

In some embodiments, the ODN is from about 8 to about 120 nucleotides in length. In particular examples, the ODN is from about 10 to about 30 nucleotides in length. Optionally, the suppressive ODN has multiple guanosine-rich sequences, for example, in certain embodiments the ODN has from about two to about 20 guanosine-rich sequences, or, more particularly, from about two to about four guanosine-rich sequences.

In one embodiment, the suppressive ODNs have a sequence comprising at least one of the human telomere-derived TTAGGG suppressive motifs (see Example 1). In some examples, the ODN has at least one TTAGGG motif, and in certain examples, the ODN has multiple TTAGGG motifs. For example, in particular examples, the ODN has from about two to about 20 TTAGGG motifs, or from about two to about four TTAGGG motifs. In this embodiment, suppressive ODNs containing multiple TTAGGG repeats are the most suppressive. Single TTAGGG motifs are suppressive only when incorporated into larger ODNs with greater than 10 bases. The TTAGGG motifs may be in either the cis or trans position, i.e., they may be present on the same or on a different strand of DNA than that expressing the stimulatory CpG sequence.

Suppression of CpG-induced immune activation requires a G-tetrad-forming sequence that imposes the two-dimensional structure necessary for G-tetrad formation. Examples of suppressive ODN include, but are not limited to, those shown in the table below:

| ODN sequence | SEQ ID NO: |
|---|---|
| CCTCAAGCTT GAGGGG | SEQ ID NO: 1 |
| TTAGGGTTAG GGTTAGGGTT AGGG | SEQ ID NO: 2 |
| TTAGGGTTAG GGTTAGGG | SEQ ID NO: 3 |
| TTAGGGTTAG GG | SEQ ID NO: 4 |
| TGGGCGGTTG GGCGGTTGGG CGGT | SEQ ID NO: 5 |
| TGGGCGGTTG GGCGGT | SEQ ID NO: 6 |
| TCAACCTTCA TTAGGG | SEQ ID NO: 7 |
| TTAGGGTTAG GGTCAACCTT CA | SEQ ID NO: 8 |
| TCAACCTTCA TTAGGGTTAG GG | SEQ ID NO: 9 |
| GGGTTAGGGT TATCAACCTT CA | SEQ ID NO: 10 |
| TCAACCTTCA GGGTTAGGGT TA | SEQ ID NO: 11 |
| GGGTGGGTGG GTATTACCAT TA | SEQ ID NO: 12 |
| ATTACCATTA GGGTGGGTGG GT | SEQ ID NO: 13 |
| TGGGCGGTTC AAGCTTGA | SEQ ID NO: 14 |
| TCAAGCTTCA TGGGCGGT | SEQ ID NO: 15 |
| GGGTGGGTGG GTAGACGTTA CC | SEQ ID NO: 16 |
| GGGGGGTCAA GCTTCA | SEQ ID NO: 17 |
| TCAAGCTTCA GGGGGG | SEQ ID NO: 18 |
| GGGGGGTCAA CGTTCA | SEQ ID NO: 19 |
| GAGCAAGCTG GACCTTCCAT | SEQ ID NO: 20 |
| GAGCAAGCTG GTAGACGTTA G | SEQ ID NO: 21 |
| GGGCAAGCTG GACCTGGGGG | SEQ ID NO: 22 |
| GGGGAAGCTG GACCTGGGGG | SEQ ID NO: 23 |
| GGGCAAGCTG GACCTTCGGG | SEQ ID NO: 24 |
| GGCAAGCTGG ACCTTCGGGG GG | SEQ ID NO: 25 |

However, any oligonucleotide capable of forming G-tetrads may be used to suppress CpG DNA-induced immune activation. In particular examples, the ODN has a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, and SEQ ID NO: 25.

Furthermore, in particular embodiments, the ODN is modified to prevent degradation. In one embodiment, suppressive ODNs can include modified nucleotides to confer resistance to degradation. Without being bound by theory, modified nucleotides can be included to increase the stability of a suppressive ODN. Thus, because phosphorothioate-modified nucleotides confer resistance to exonuclease digestion, the suppressive ODNs are "stabilized" by incorporating phosphorothioate-modified nucleotides.

In some embodiments, the ODN has a phosphate backbone modification, and in particular examples, the phosphate backbone modification is a phosphorothioate backbone modification. In one embodiment, the guanosine-rich sequence and its immediate flanking regions include phosphodiester rather than phosphorothioate nucleotides. In one specific non-limiting example, the sequence TTAGGG includes phosphodiester bases. In some examples, all of the bases in an ODN are phosphodiester bases. In other examples, the ODN is a phosphorothioate/phosphodiester chimera.

As disclosed herein, any suitable modification can be used to render the ODN resistant to degradation in vivo (e.g., via an exo- or endo-nuclease). In one specific, non-limiting example, a modification that renders the ODN less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). ODNs containing a diol, such as tetraethyleneglycol or hexaethyleneglycol, at either or both termini, have also been shown to be more resistant to degradation.

The suppressive ODN of the disclosure can be synthesized by standard methods well known in the art. Most commonly, synthesis is performed on an oligonucleotide synthesizer using the standard cyanoethyl phosphoramidite chemistry. These include, but are not limited to, phosphodiester, phosphorothioate, peptide nucleic acids, synthetic peptide analogs, and any combination thereof. Those skilled in the art will recognize that any other standard technique may be used to synthesize the suppressive ODN described herein.

In one embodiment, a suppressive ODN is included in a delivery complex. The delivery complex can include the suppressive ODN and a targeting means. Any suitable targeting means can be used. For example, in some embodiments, a suppressive ODN is associated with (e.g., ionically or covalently bound to, or encapsulated within) a targeting means (e.g., a molecule that results in higher affinity binding to a target cell, such as a B cell). A variety of coupling or cross-linking agents can be used to form the delivery complex, such as protein A, carbodiamide, and N-succinimidyl-3-(2-pyridyldithio) propionate (SPDP). Examples of oligodeoxynucleotide delivery complexes include a suppressive ODN associated with a sterol (e.g., cholesterol), a lipid (e.g., a cationic lipid, anionic lipid, virosome or liposome), and a target cell specific binding agent (e.g., a ligand recognized by target cell specific receptor). Without being bound by theory, the complex is sufficiently stable in vivo to prevent significant uncoupling prior to delivery to the target cell. In one embodiment, the delivery complex is cleavable such that the ODN is released in a functional form at the target cells.

B. Methods for Treating Uveitis and Pharmaceutical Compositions

A method is disclosed herein for the treatment of uveitis in a subject by administering a therapeutically effective amount of a suppressive ODN, thereby treating the subject. Any form of uveitis can be treated using suppressive ODNs. For example, iritis, cyclitis, panuveits, iridocyclitis, posterior uveitis, anterior uveitis and diffuse uveitis can be treated using the methods disclosed herein. Anterior and/or posterior uveitis can be treated using the suppressive ODNs. Both acute onset uveitis and chronic uveitis also can be treated.

In one embodiment, a method is provided for treating anterior uveitis in a subject. Subjects can be treated that are affected with idiopathic iridocyclitis, HLA-B27 positive iridocyclitis, uveitis associated with juvenile rheumatoid arthritis, Fuch's heterochromatice iridocyclitis, herpes simplex keatovueitis, ankylosing spondylitis, intraocular lens related uveitis, Reiter's syndrome, Herpes zoster keratouveitis, uveitis associated with syphilis, traumatic iridocyclitis, uveitis associated with inflammatory bowel disease, tuberculosis iridocyclitis.

In another embodiment, a method is provided for treating posterior uveitis in a subject. Thus subjects can be treated that are affected with toxoplasma retinochroiditis, retinal vasculitis, idiopathic posterior uveitis, ocular histoplasmosis, toxocariasis, cytomegalovirus retinitis, idiopathic retinitis, serpinous choroidopathy, acute multifocal placoid, pigment eptiheliopathy, acute retinal necrosis, bird shot choroidopathy, uveitis associated with a leukemia or a lymphoma, reticulum cell sarcoma, ocular candidiasis, tuberculous uveitis, lupus retinitis.

In a further embodiment, a method is provided for treating diffuse uveitis. Thus, subjects can be treated that are affected with sarcoidosis, syphilis, Vogt-Koyanagi-Harada syndrome, or Bechet's disease.

In one embodiment, a sign or a symptom of the uveitis is decreased or alleviated. Ocular signs include ciliary injection, aqueous flare, the accumulation of cells visible on ophthalmic examination, such as aqueous cells, retrolental cells, and vitreous cells, keratic precipitates, and hypema Symptoms include pain (such as ciliary spasm), redness, photophobia, increased lacrimation, and decreased vision. One of skill in the art can readily diagnose uveitis. In one embodiment, biomicroscopy (for example, a "slit lamp") is used to diagnose uveitis, to evaluate the clinical course of the disease or to verify that a treatment protocol has been successful.

Administration of the suppressive ODN can be systemic or local. One ODN, or multiple ODNs can be utilized.

The suppressive ODNs described herein can be formulated in a variety of ways depending on the location and type of disease to be treated. Pharmaceutical compositions are thus provided for both local use (for example, topical or within an ocular transplant), as well as for systemic use. The subject can be any subject, such as a mammalian subject. Therefore, the disclosure includes within its scope pharmaceutical compositions comprising at least one suppressive ODN formulated for use in human or veterinary medicine.

Pharmaceutical compositions that include at least one suppressive ODN as described herein as an active ingredient, or that include both a suppressive ODN and an additional agent as active ingredients, can be formulated with an appropriate solid or liquid carrier, depending upon the particular mode of administration chosen.

The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical and oral formulations can be employed. Topical preparations can include eye drops, ointments, sprays and the like. Eye drops or sprays can be provided in unit dose dispensers (such as eye drop bottles that dispense a metered unit dose that contains the suppressive ODN either alone or in combination with other therapeutic agents such as corticosteroids). Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art. Implants can also be employed (see below).

The pharmaceutical compositions that include a suppressive ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The suppressive ODN can be formulated with additional therapeutic agents. Exemplary agents include cyclosporine, FK506, steroids such as hydrocortisone, antibodies (such as anti-CD4 or antibodies that specifically bind the IL-2 receptor), cytokines (such as beta-interferon), or non-steroidal anti-inflammatory agents. Additional agents include antibacterial antibiotics, such as minoglycosides (for example, amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (for example, azidamfenicol, chloramphenicol, florfenicol, thiamphenicol), ansamycins (for example, rifamide, rifampin, rifamycin sv, rifapentine, rifaximin), β-lactams (for example, carbacephems (e.g., loracarbef), carbapenems (for example, biapenem, imipenem, meropenem, panipenem), cephalosporins (for example, cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoximne, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (for example, cefbuperazone, cefmetazole, cefininox, cefotetan, cefoxitin), monobactams (for example, aztreonam, carumonam, tigemonam), oxacephems, flomoxef, moxalactam), penicillins (for example, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin g benzathine, penicillin g benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), other (for example, ritipenem), lincosamides (for example, clindamycin, lincomycin), macrolides (for example, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (for example, amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (for example, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin). Agents of use also include synthetic antibacterials, such as 2,4-Diaminopyrimidines (for example, brodimoprim, tetroxoprim, trimethoprim), nitrofurans (for example, furaltadone, furazolium chloride, nifuradene, nifuratel, nifurfoline, nifurpirinol, nifurprazine, nifurtoinol, nitrofirantoin), quinolones and analogs (for example, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (for example, acetyl sulfamethoxypyrazine, benzylsulfamide, chloramine-b, chloramine-t, dichloramine t, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (for example, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (for example, clofoctol, hexedine, methenamine, methenamine anhydromethylene-citrate, methenamine hippurate, methenamine mandelate, methenamine sulfosalicylate, nitroxoline, taurolidine, xibornol). Additional agents of use include antifungal antibiotics such as polyenes (for example, amphotericin B, candicidin, dennostatin, filipin, fungichromin, hachimycin, hamycin, lucensomycin, mepartricin, natamycin, nystatin, pecilocin, perimycin), others (for example, azaserine, griseofulvin, oligomycins, neomycin undecylenate, pyrrolnitrin, siccanin, tubercidin, viridin) allylamines (for example, butenafine, naftifine, terbinafine), imidazoles (for example, bifonazole, butoconazole, chlordantoin, chlormiidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (for example, tolciclate, tolindate, tolnaftate), triazoles (for example, fluconazole, itraconazole, sapercona-zole, terconazole) others (for example, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate). Antineoplastic agents can also be of use including (1) antibiotics and analogs (for example, aclacinomycins, actinomycin, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), (2) antimetabolites such as folic acid analogs (for example, denopterin, edatrexate, methotrexate, piritrexim, pteropterin, Tomudex®™, trimetrexate), (3) purine analogs (for example, cladribine, fludarabine, 6-mercaptopurine, thiamiprine, thioguanine), (4) pyrimidine analogs (for example, ancitabine, azacitidine, 6-azauridine, carmofur, cytarabine, doxifluridine, emitefur, enocitabine, floxuridine, fluorouracil, gemcitabine, tagafur).

Steroidal anti-inflammatory agents can also be included such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, cyclosporine, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone firoate, paramethasone, prednicarbate, prednisolone, prednisolone 25-diethylanino-acetate, prednisolone sodium phosphate, prednisone, prednival, prednylidene, rimexolone, tixocortol, triamcinolone, triamcinolone acetonide, triamcinolone benetonide, and triamcinolone hexacetonide. In addition, non-steroidal anti-inflammatory agents can be used. These include aminoarylcarboxylic acid derivatives (for example, enfenamic acid, etofenamate, flufenamic acid, isonixin, meclofenamic acid, mefenamic acid, niflumic acid, talniflumate, terofenamate, tolfenamic acid), arylacetic acid derivatives (for example, aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (for example, bumadizon, butibufen, fenbufen, xenbucin), arylcarboxylic acids (for example, clidanac, ketorolac, tinoridine), arylpropionic acid derivatives (for example, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (for example, difenamizole, epirizole), pyrazolones (for example, apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (for example, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (for example, ampiroxicam, droxicam, isoxicam, lomoxicam, piroxicam, tenoxicam), epsilon.-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

The suppressive ODN can be included in an inert matrix for either topical application or injection into the eye, such as for intra-vitreal administration. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including a suppressive ODN can be applied topically, either in the form of drops or as an aqueous based cream, or can be injected intraocularly. In a formulation for topical application, the ODN is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the ODN over time. In one example, the suppressive ODN can be dissolved in an organic solvent such as DMSO or alcohol as previously described and contain a polyanhydride, poly(glycolic) acid, poly(lactic) acid, or polycaprolactone polymer.

The ODN can be included in a delivery system that can be implanted at various sites in the eye, depending on the size, shape and formulation of the implant, and the type of transplant procedure. The ODN can be used alone. However, in another embodiment, at least one additional agent, such as at least one agent that is described above, can be included along with the ODN in the delivery system, such as in an implant. The delivery system is then introduced into the eye. Suitable sites include but are not limited to the anterior chamber, anterior segment, posterior chamber, posterior segment, vitreous cavity, suprachoroidal space, subconjunctiva, episcleral, intracorneal, epicorneal and sclera. In one example, the ODN delivery system is placed in the anterior chamber of the eye. In another example, the ODN delivery system is placed in the vitreous cavity.

The implants can be inserted into the eye by a variety of methods, including placement by forceps or by trocar following making an incision in the sclera (for example, a 2-3 mm incision) or other suitable site. In some cases, the implant can be placed by trocar without making a separate incision, but instead by forming a hole directly into the eye with the trocar. The method of placement can influence the release kinetics. For example, implanting the device into the vitreous or the posterior chamber with a trocar may result in placement of the device deeper within the vitreous than placement by forceps, which may result in the implant being closer to the edge of the vitreous. The location of the implanted device may influence the concentration gradients of ODN surrounding the device, and thus influence the release rates (for example, a device placed closer to the edge of the vitreous may result in a slower release rate, see U.S. Pat. No. 5,869,079 and U.S. Pat. No. 6,699,493).

The suppressive agent is delivered for a sufficient time period to achieve the desired effect. Thus, in one embodiment, the suppressive ODN is delivered for at least about 2 days, such as for about five days, seven days, ten days, 14 or 21 days. In several embodiments, the immunosuppressive agent is delivered for at least about one week, at least about two weeks, at least about three weeks, at least about four weeks, at least about five weeks, at least about six weeks, at least about seven weeks, at least about eight weeks, at least about nine weeks, at least about 10 weeks, and at least about 12 weeks. In one embodiment, extended periods of delivery are achieved with the use of an implant. The duration of use of a suppressive ODN can be the medical history of the patient and other contributing factors (such as use of other agents, etc.). If extended periods of administration are required, the suppressive ODN can be administered for up to six months, or one year, or longer. In one embodiment, for extended release, an implant is utilized. More than one implant can also be utilized. For example, implants can be sequentially implanted into the vitreous in order to maintain concentrations for even long periods. In one embodiment, more than one implant can be sequentially implanted into the eye in order to maintain therapeutic drug concentrations for longer periods.

The use of implants is well known in the art (see U.S. Pat. No. 6,699,493 and U.S. Pat. No. 5,869,079). In one embodiment, an implant is formulated with the suppressive ODN associated with a bioerodible polymer matrix. Additional agents can be included with the suppressive ODN such as dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, and prednisolone.

Generally, when implants are used, the suppressive ODN is homogeneously distributed through the polymeric matrix, such that it is distributed evenly enough that no detrimental fluctuations in rate of release occur because of uneven distribution of the immunosuppressive agent in the polymer matrix. The selection of the polymeric composition to be employed varies with the desired release kinetics, the location of the implant, patient tolerance, and the nature of the implant procedure. The polymer can be included as at least about 10 weight percent of the implant. In one example, the polymer is included as at least about 20 weight percent of the implant. In another embodiment, the implant comprises more than one polymer. These factors are described in detail in U.S. Pat. No. 6,699,493. Characteristics of the polymers generally include biodegradability at the site of implantation, compatibility with the agent of interest, ease of encapsulation, and water insolubility, amongst others. Generally, the polymeric matrix is not fully degraded until the drug load has been released. The chemical composition of suitable polymers is known in the art (for example, see U.S. Pat. No. 6,699,493).

The suppressive ODNs described herein can be formulated in an implantable form with other carriers and solvents. For example, buffering agents and preservatives can be employed. Water soluble preservatives include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents can be present in individual amounts of from about 0.001 to about 5% by weight, such as about 0.01 to about 2%. Suitable water soluble buffering agents that may be employed are sodium carbonate, sodium borate, sodium phosphate, sodium acetate, sodium bicarbonate. These agents can be present in amounts sufficient to maintain a pH of the system of between about 2 to about 9 such as about 4 to about 8, or at about 6 to about 7. In one example, the pH of the system is maintained at about 7. As such, the buffering agent can be as much as 5% on a weight-to-weight basis of the total composition. Electrolytes such as sodium chloride and potassium chloride may also be included in the formulation. The proportions of suppressive ODN, polymer, and any other modifiers may be empirically determined by formulating several implants with varying proportions. A USP approved method for dissolution or release test can be used to measure the rate of release (USP 23; NF 18 (1995) pp. 1790-1798). The implant sizes and shape can also be varied for use in particular regions of the eye (see U.S. Pat. No. 5,869,079).

The disclosure is illustrated by the following non-limiting Examples.

EXAMPLES

Example 1

Material and Methods

Immunization:
Female B 10.A mice were immunized subcutaneously with 40 ug bovine IRBP, emulsified with CFA containing 2.5 mg/ml *Mycobacterium tuberculosis* strain H37RA in a total volume of 0.2 ml, divided between the base of the tail and the two thighs. Pertussis toxin (0.25 ug/mouse) was also given as an adjuvant, in a volume of 0.1 ml, administered intraperitoneally (i.p.).

Treatment:
Immunized mice were treated, i.p., with suppressive ODN (A151, SEQ D NO: 2), control ODN 1471, (which has the sequence TCAAGCTTGA, SEQ ID NO: 26), or PBS on days 0, 3, 7, 11. Both ODNs were given each time at 300 ug/mouse.

Disease Assessment:
Mice were sacrificed on day 14 post-immunization and the severity of ocular inflammation was scored on a scale of 0-4 as detailed by Chan et al. (*J Autoimmun.* 3:247, 1990).

Immune Responses:
Cellular immune responses were measured by a conventional lymphocyte proliferation assay, using the draining lymph nodes of the immunized mice. Release of cytokines by these lymphocytes was determined by measuring the levels of interferon-gamma and interleukin-4 in culture supernatants following incubation for 48 hours with IRBP, or purified protein derivative (PPD).

The cytokine levels were determined by ELISA.

Example 2

Effect of ODN Administration on the Inflammatory Response

Figure 2:
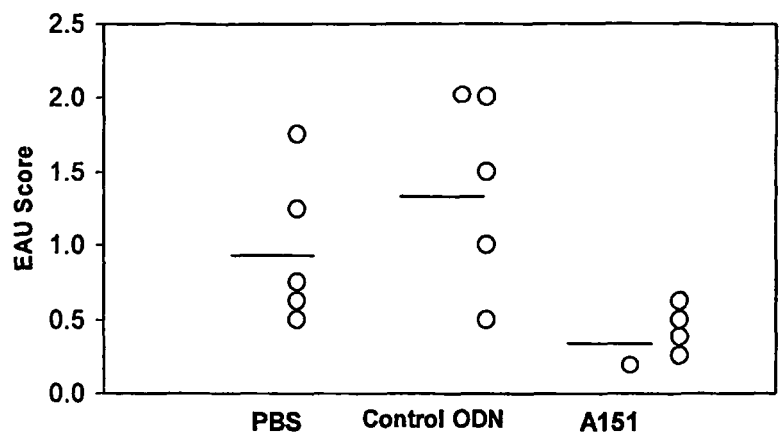
FIG. 2 is a graph of the EAU score following treatment with phosphate buffered saline (PBS), a control oligonucleotide (ODN), or A151. Histological scores were evaluated on day 14 post-immunization. The horizontal bars show the average of histology scores of eyes in each group. Treatment with A151 resulted in a lower EAU score, documenting decreased disease severity following administration of this suppressive ODN.

FIG. 2 shows the effect of treatment with suppressive ODN on the frequency and severity with which EAU develops in B10. A mice treated as described in Example 1. All animals receiving the sham treatment (PBS or control ODN) developed disease with an EAU score ≥0.5, whereas ⅗ mice treated with suppressive ODN did not develop disease. The average disease score of the animals treated with suppressive ODN was <0.05, and was at least 3-fold lower than that of either control group.

Figure 3:
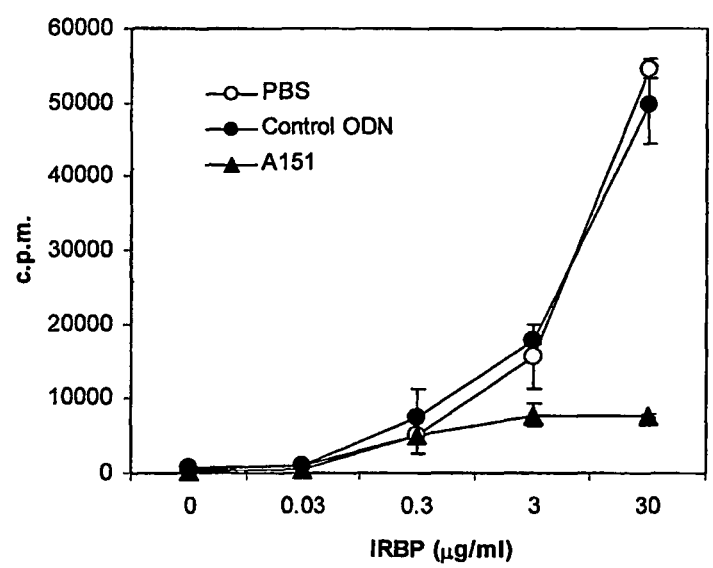
FIG. 3 is a line graph showing the T cell proliferation (measured as counts per minute (c.p.m.)) following treatment with phosphate buffered saline (PBS), a control oligonucleotide (ODN), or A151. Draining lymph nodes were collected on 14 days post-immunization and pooled for each group. Cells were tested for proliferation against IRBP at different concentrations, using conventional methods. Cultures consisted of 400,000 lymph node cells, in 0.2 ml RPMI-1640 medium supplemented with HL-1 (serum replacement), 2-mercaptoethanol and antibiotics, in 96 well microplates. In brief, the cultures, in triplicate, were incubated for a total of 92 hours and were pulsed with 3H-thymidine, 0.5 uCi per well, for the last 16 hours. The cells were collected on filtermates, using a Brandel harvester and the radioactivity was measured by a 1450 Microbeta counter (Perkin-Elmer). The data are presented as mean delta CPM (=counts in cultures with antigen minus counts in control cultures). A response was seen following stimulation with more than 0.3 µg/ml of interphotoreceptor retinoid binding protein (IRBP).

FIG. 3 shows that spleen cells from mice injected with IRBP (see Example 1) proliferate strongly when cultured with IRBP in vitro, unless the animals were co-treated with suppressive ODN A151.

Figure 4:
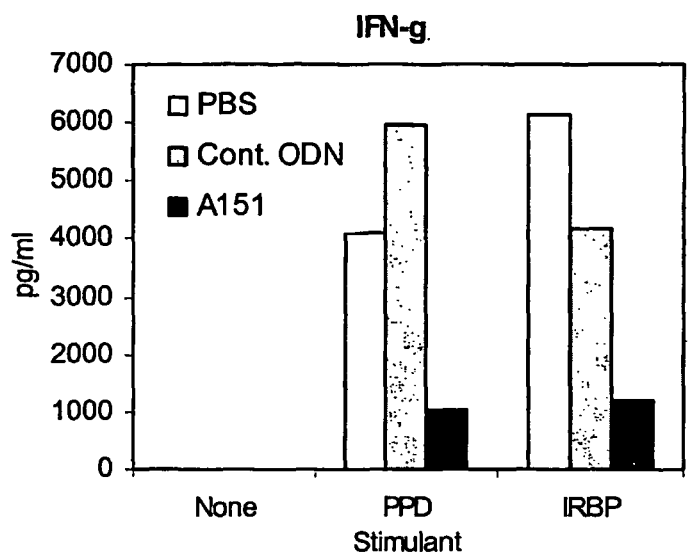
FIG. 4 is a bar graph of interferon gamma (IFN-g) expression following treatment with PBS, a control ODN, or A151. Draining lymph nodes were collected on day 14 and stimulated in vitro with IRBP (30 ug/ml) or purified protein derivative, PPD (5 ug/ml). Supernatants were collected after 48 hours and cytokine levels were measured by ELISA. Administration of A151 resulted in decreased expression of IFN-g.

FIG. 4 shows that spleen cells from mice injected with IRBP (see Example 1) produce large amounts of the Th1 cytokine IFN-g when cultured with PPD or IRBP in vitro, unless the animals were co-treated with suppressive ODN A151. These findings demonstrate that suppressive ODNs reduce the immune response elicited against both IRBP and co-administered antigens.

Figure 5:
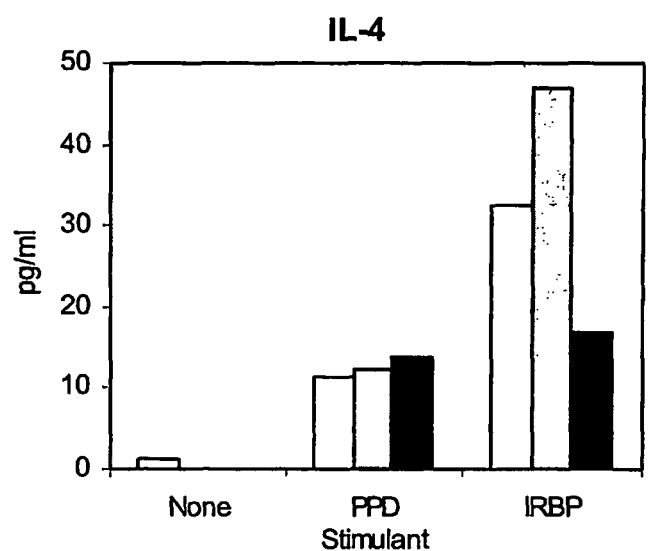
FIG. 5 is a bar graph of interleukin-4 (IL-4) expression following treatment with PBS, a control ODN, or A151. Draining lymph nodes were collected on day 14 and stimulated in vitro with IRBP (30 ug/ml) or purified protein derivative (PPD, 5 ug/ml). Supernatants were collected after 48 hours and cytokine levels were measured by ELISA. Administration of A151 resulted in decreased expression of IL-4.

FIG. 5 shows that spleen cells from mice injected with IRBP (see Example 1) produce large amounts of the Th2 cytokine IL-4 when cultured IRBP in vitro, unless the animals were co-treated with suppressive ODN A151. These findings demonstrate that suppressive ODN reduce both Th1 and Th2 responses induced by IRBP in vivo.

Example 3

Effect of Suppressor ODN on Adoptively Transferred Ocular Inflammation

Methods (i) Disease Induction:

Transgenic mice expressing hen egg lysozyme (HEL) in their lens (under control of the alphaA crystallin promoter) were injected with T-helper type 1 lymphocytes specific against HEL, at the indicated numbers. The eyes were collected on day 7 post cell injection and the eyes were examined histologically for inflammatory changes (see S. Kim et al., *Invest. Ophthalmol. Vis. Sci.,* 43:758, 2002, herein incorporated by reference).

(ii) Treatment with Suppressive ODN:

A151, dissolved in phosphate buffered saline (PBS), was injected intraperitoneally on days 0 and 3 after T cell transfer. Control mice were injected with PBS alone.

Figures 6A, 6B:
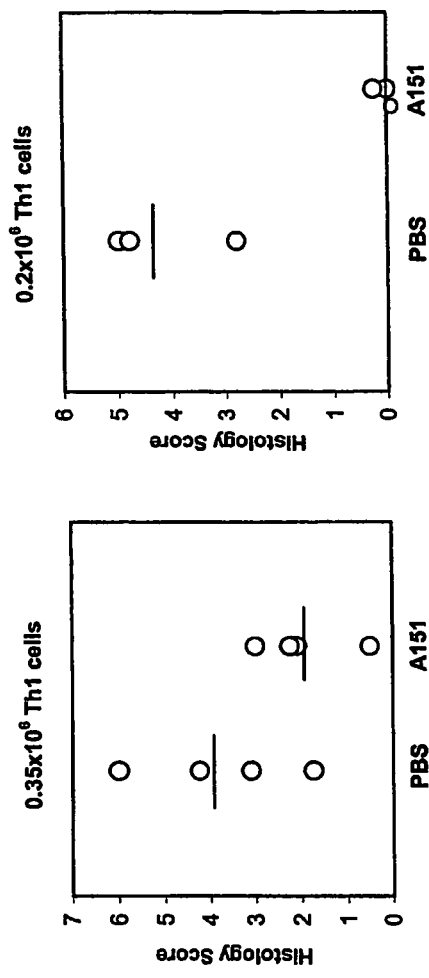
FIGS. 6A and 6B are two graphs demonstrating the effect of suppressive ODN on adoptively transferred uveitis.

Results:

Two experiments were performed, using 350,000 cells/mouse in the first experiment and 200,000 cells/mouse in the second experiment. As shown in FIGS. 6A and 6B, treatment with A151 inhibited the inflammatory process, with a higher level of inhibition seen in the second experiment, in which fewer cells were injected.

These results show that suppressive ODN can affect the efferent limb of the pathogenic immune response. Without being bound by theory, suppressive ODN can inhibit the proliferation of the adoptively transferred cells.

It will be apparent that the precise details of the methods or compositions described may be varied or modified without departing from the spirit of the described invention. We claim all such modifications and variations that fall within the scope and spirit of the claims below.

The invention claimed is:

1. A method of reducing uveitis in a subject, comprising selecting an isolated oligodeoxynucleotide consisting of the nucleic acid sequence set forth as SEQ ID NO: 2; and systemically or intraocularly administering to the subject in need thereof a therapeutically effective amount of a composition comprising the selected isolated oligodeoxynucleotide and a pharmaceutically acceptable carrier to suppress production of interleukin (IL-4) and interferon gamma, and thereby reducing ocular inflammation in the subject.

2. The method of claim 1, wherein the oligodeoxynucleotide is administered systemically.

3. The method of claim 1, wherein the uveitis comprises anterior or posterior uveitis.

4. The method of claim 1, wherein the uveitis comprises diffuse uveits.

5. The method of claim 1, wherein the uveitis comprises at least one of cyclitis, pars planitis, chorioretinitis (inflammation of the choroid), iridocyclitis, or iritis.

6. The method of claim 1, further comprising administering a therapeutically effective amount of an additional anti-inflammatory agent.

7. The method of claim 1, further comprising administering a therapeutically effective amount of an additional non-nucleotide immunosuppressive agent.

8. The method of claim 1, further comprising administering a therapeutically effective amount of an antibacterial or an antifungal agent.

9. The method of claim 1, wherein the uveitis is a result of surgical or traumatic injury to the eye.

10. The method of claim 1, wherein the uveitis is a result of an autoimmune disorder.

11. The method of claim 1, wherein the uveitis is a result of an infection.

12. The method of claim 1, wherein the composition is administered intraocularly by administering the therapeutically effective amount of the oligonucleotide topically to the eye.

13. The method of claim 1, wherein the composition is administered intraocularly by intravitreal administration.

14. The method of claim 1, wherein the composition is administered intraocularly by implantation.

15. The method of claim 1, further comprising measuring the production of IL-4, interferon gamma or both by lymphocytes from the subject.

16. The method of claim 1, wherein the oligodeoxynucleotide is modified to prevent degradation.

17. The method of claim 16, wherein the oligodeoxynucleotide comprises a phosphodiester modification.

* * * * *